United States Patent [19]

Hattler

[11] Patent Number: 5,271,743
[45] Date of Patent: Dec. 21, 1993

[54] SYSTEM TO OPTIMIZE THE TRANSFER OF GAS THROUGH MEMBRANES

[76] Inventor: Brack G. Hattler, 5226 Westminster Pl., Pittsburgh, Pa. 15232

[21] Appl. No.: 878,750

[22] Filed: May 5, 1992

Related U.S. Application Data

[63] Continuation-in-part of Ser. No. 676,262, Mar. 27, 1991, Pat. No. 5,122,113.

[51] Int. Cl.$^5$ ............................................. A61M 37/00
[52] U.S. Cl. ........................................... 604/26; 623/1; 623/12
[58] Field of Search ..................... 604/23–26, 604/48, 49, 52–53; 128/DIG. 3; 623/1, 9, 12; 261/DIG. 28, 122

[56] References Cited

U.S. PATENT DOCUMENTS

| | | | |
|---|---|---|---|
| 3,505,686 | 4/1970 | Bodell | 3/1 |
| 4,583,969 | 4/1986 | Mortensen | 604/49 |
| 4,631,053 | 12/1986 | Taheri | 604/49 |
| 4,671,287 | 6/1987 | Fiddian-Green | 604/26 |
| 4,850,958 | 7/1989 | Berry et al. | 604/53 |
| 4,911,689 | 3/1990 | Hattler | 604/26 |
| 4,950,224 | 8/1990 | Gorsuch et al. | 604/4 |
| 4,986,809 | 1/1991 | Hattler et al. | 604/26 |
| 5,037,383 | 8/1991 | Vaslef et al. | 604/26 |

OTHER PUBLICATIONS

International Patent Application No. PCT/US90/07165 (Publ. No. WO 91/09642) Filing Date: Dec. 6, 1990 Title: Apparatus and Method for Furling and Introducing An Extrapulmonary Blood Gas etc., Cardiopulmonics.
Wampler, "An Axial Flow Ventricular Assist Device With Integrated Motor Drive".
Butler et al., "Development of An Implantable Axial Flow LVAS".
Jegaden et al., "Temporary left ventricular assistance with a Homopump assist device during acute myocardial infarction".
Shiiya et al., "Effects of Hemopump Support on Left Ventricular Unloading and Coronary Blood Flow".

Primary Examiner—C. Fred Rosenbaum
Assistant Examiner—Michael Rafa
Attorney, Agent, or Firm—Gary M. Polumbus

[57] ABSTRACT

A percutaneous intravenous oxygenator includes a plurality of hollow gas permeable fibers formed into a plurality of loops with one end of the fiber loops being connected to a source of oxygen while the opposite end is connected to a vacuum source. The oxygenator is insertable into a blood vessel such that when oxygen is drawn into the fiber loops, it will diffuse through the walls of the fibers into oxygen deficient blood passing thereby while excess carbon dioxide in the blood will pass in a reverse or cross diffusion pattern through the walls of the fibers into the interior thereof for removal from the fiber loops by the vacuum source. Two separate embodiments for moving the fibers to prevent streaming of blood past the oxygenator are disclosed for optimal cross diffusion of the gases. In one embodiment, a rotatable blade is disclosed within the looped fibers so as to disrupt the linear flow of blood and direct it radially outwardly in convective swirling fashion to keep the fibers moving and optimally disposed for maximum gas diffusion. In the second embodiment, an electromagnet is disclosed within the loops of fibers and the fibers themselves carry a paramagnetic material so that the fibers can be selectively attracted to the rod or actively or passively repelled from the rod again to keep the fibers in motion to prevent streaming of the blood and to optimize the cross transfusion of gases.

18 Claims, 6 Drawing Sheets

Fig_12

Fig_13

Fig_11

SYSTEM TO OPTIMIZE THE TRANSFER OF GAS THROUGH MEMBRANES

CROSS-REFERENCE TO RELATED APPLICATION

This application is a continuation-in-part of applicant's co-pending U.S. patent application Ser. No. 07/676,262, entitled "Inflatable Percutaneous Oxygenator" filed on Mar. 27, 1991, U.S. Pat. No. 5,122,113.

BACKGROUND OF THE INVENTION

1. Field of the Invention

The present invention relates generally to the field of oxygenators used to increase the oxygen level in a patient's blood. More particularly, the present invention relates to a percutaneous oxygenator having a plurality of gas permeable fiber membranes that can be positioned within a blood containing cavity of a patient's body (e.g. in the inferior vena cava, superior vena cava, the right atrium of the heart, or any combination thereof) and includes a system for optimizing the exposure of the surface area of said fibers to a patient's blood while minimizing streaming of the blood flow around the fibers and thereby maximizing the cross-diffusion of oxygen and carbon dioxide through the walls of said fibers.

2. Statement of the Problem

Many types of blood oxygenators are well known in the art. For example, during open heart surgery, the patient is interconnected with an external oxygenator, commonly known as a heart-lung machine, which introduces oxygen into the blood system. Most types of oxygenators use a gas-permeable membrane. Blood flows along one side of the membrane, and oxygen is supplied to the other side of the membrane. Given a sufficient pressure gradient between the oxygen supply and the blood, the oxygen will diffuse through the membrane and into the blood. In addition, carbon dioxide in the blood will tend to diffuse from the blood into the interior of the membrane.

In other situations, a smaller, implantable oxygenator may be sufficient to adequately supplement the patient's cardiopulmonary function by marginally increasing the oxygen content of the patient's blood. For example, patients suffering from emphysema, pneumonia, congestive heart failure, or other chronic lung disease often have blood oxygen partial pressures of approximately 40 torr. A relatively small increase of 10% to 20% is generally sufficient to adequately maintain the patient. An implantable oxygenator is a particularly desirable alternative in that it avoids the need to intubate the patient in such cases. In addition, temporary use of an implantable oxygenator is sufficient in many cases to tide the patient over an acute respiratory insult. Placing such patients on a conventional respirator is often the beginning of a progressive downhill spiral by damaging the patient's pulmonary tree and thereby causing greater dependence on the respirator.

Implantable oxygenators typically include a plurality of hollow gas permeable membrane fibers which form a loop so that oxygen can be fed into one end of a fiber and $CO_2$ removed from the other end as a result of the cross-diffusion that takes place. The effective rate of diffusion in implantable oxygenators can be limited in some instances by the problem of "streaming" or "channeling", wherein the blood stream establishes relatively stable patterns of flow around and through the oxygenator. Portions of the fibers are exposed to a relatively high velocity, turbulent flow of blood. These conditions tend to increase cross-diffusion of oxygen and carbon dioxide. However, other portions of the fibers are exposed to a low velocity, laminar flow of blood which reduces diffusion of gases. Those portions of the fibers immediately adjacent to the regions of high blood flow may continue to experience high rates of diffusion, but the remaining portions of the fibers tend to have relatively low diffusion rates. Thus, the overall diffusion rate of the oxygenator can be substantially diminished by streaming.

A number of devices and processes have been invented in the past relating to different types of oxygenators, including the following:

| Inventor | Pat. No. | Issue Date |
| --- | --- | --- |
| Bodell | 3,505,686 | Apr. 14, 1970 |
| Burton | 4,159,720 | July 3, 1979 |
| Kopp, et al. | 4,346,006 | Aug. 24, 1982 |
| Mortensen | 4,583,969 | Apr. 22, 1986 |
| Taheri | 4,631,053 | Dec. 23, 1986 |
| Kitagawa, et al. | 4,743,250 | May 10, 1988 |
| Berry, et al. | 4,850,958 | July 25, 1989 |
| Hattler | 4,911,689 | Mar. 27, 1990 |
| Hattler, et al. | 4,986,809 | Jan. 22, 1991 |

Tanishita, et al., "Augmentation of Gas Transfer with Pulsatile Flow in the Coiled Tube Member Oxygenator Design", 26 Trans. Am. Soc. Artif. Intern. Organs 561 (1980).

Bodell demonstrates the general concept of using gas-permeable fibers to boost the oxygen level of blood. FIGS. 6 and 10 show two variations of this device intended for use inside the body of the patient. In the implantable embodiment of the Bodell device, a tubular casing serves as a shunt either from the pulmonary artery to the left atrium of the heart (FIG. 6), or more generally between an artery and a vein (FIG. 10). A multitude of parallel-connected capillary tubes are used to oxygenate and/or purify the blood circulating through the casing.

FIGS. 3-5 of the Mortensen patent show a transvenous oxygenator made of a plurality of small diameter gas-permeable tubes 32 connected to headers 34 and 36 at each end. However, the specific device disclosed by Mortensen has a significant disadvantage in that two incisions are required. The insertion process is also rather complex.

Taheri discloses a transvenous oxygenator having a single membrane 16 through which oxygen diffuses. The membrane is disposed within a sheath 18 and both are supported by a flexible wire 20.

Berry, et al., disclose an in vivo extrapulmonary blood gas exchange device having a bundle of elongated gas permeable tubes 12 bound at each end and enclose within respective air-tight proximal and distal chambers 28 and 30. A dual lumen tube is situated relative to the gas-permeable tubes such that an outer lumen terminates within the proximal chamber 28 and an inner lumen terminates within the distal chamber 30.

The Hattler patents disclose several embodiments of percutaneous oxygenators. In the simplest embodiment ('689), oxygen is circulated through a plurality of hollow, gas-permeable fibers forming loops inserted through a single incision into a blood vessel. In other embodiments ('809), the fiber loops are bisected and placed in fluid communication with a mixing chamber within a hollow tip at the distal end of the device.

Tanishita, et al., disclose an extracorporeal oxygenator (FIGS. 1A and 1B) in which diffusion of gases was enhanced by application of pulsatile flow superimposed on a steady mean flow. Flow pulsation is introduced in the oxygenator chamber by directly vibrating its bottom plate. 1. Solution to the Problem. The problem of streaming appears not to have been recognized in prior art percutaneous oxygenators. None of the prior art references known to applicant shows a percutaneous oxygenator that includes an effective system for moving the fibers and/or disturbing the flow of blood to minimize streaming and thereby maximize cross-diffusion of gases between the patient's blood stream and the oxygenator.

SUMMARY OF THE INVENTION

The percutaneous oxygenator of the invention has a plurality of hollow gas permeable but liquid impermeable fibers that form loops and are insertable into a blood vessel. Oxygen gas is fed into one end of the fibers and $CO_2$ withdrawn from the opposite end of the fibers as a result of cross diffusion of oxygen and $CO_2$ through the fiber walls when the oxygenator is positioned within the vessel. In one embodiment of the oxygenator, a system for agitating the blood is positioned within the loops formed by the fibers so that the linear flow of blood is disrupted and the blood is directed radially outwardly by the agitator to randomly move the fibers to prevent the streaming of blood past the fibers. The blood is thereby forced into a convective flow pattern so as to optimize the surface areas of the fibers exposed to the blood thereby resulting in optimal cross-diffusion of gases through the walls of the fibers. In the preferred form of this embodiment, the liquid agitator is in the form of a rotating curved blade designed to disrupt the linear blood flow and redirect the flow into swirling radially oriented patterns which urge the fibers to continuously move thereby deterring streaming.

In another embodiment of the present invention, an elongated magnetizable rod is positioned longitudinally of the oxygenator in the center of the loops formed by the fibers and a system is employed for electrically magnetizing the rod so that it alternately attracts and actively or passively repels the fibers which have been treated to include a paramagnetic material. The paramagnetic material can either be integrated into the material from which the fibers are made or affixed to the flat fibers at spaced locations along the length thereof. The electrical system for magnetizing the rod includes a coil wrapped around a portion of the rod and interconnected with a source of electrical energy through a switching system that either alternately energizes and de-energizes the rod or alternately changes the polarity of the magnetization of the rod. In the first instance, upon energization of the coil and thus magnetization of the rod, the fibers are drawn toward the rod and upon a subsequent de-energization of the coil, the rod is in turn demagnetized and the fibers allowed to passively move away from the rod into a naturally spaced relationship with the rod. In the latter instance, polarization of the magnet in one direction will attract the fibers to the magnetized rod and a reverse polarization will repel the fibers so that they are forcefully moved toward and away from the rod to prevent streaming of blood past the oxygenator.

Other aspects, features and details of the present invention can be more completely understood by reference to the following detailed description of a preferred embodiment, taken in conjunction with the drawings and from the appended claims.

BRIEF DESCRIPTION OF THE DRAWINGS

The present invention can be more readily understood in conjunction with the accompanying drawings, in which.

DETAILED DESCRIPTION OF THE INVENTION

Figures 1, 2, 3:
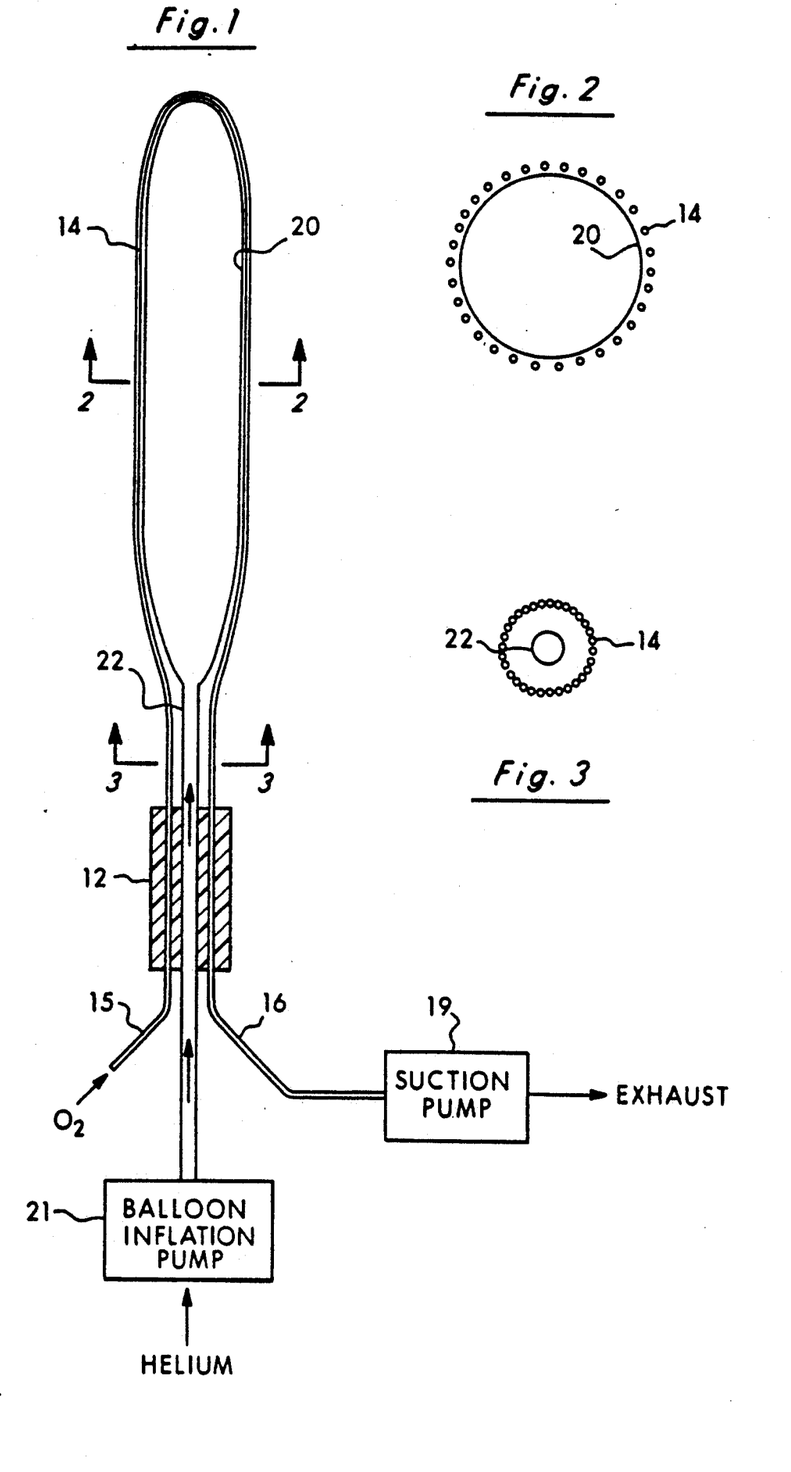
FIG. 1 is a side cross-sectional view of one embodiment of the present invention with the balloon inflated.
FIG. 2 is another cross-sectional view taken along plane 2—2 of FIG. 1.
FIG. 3 is yet another cross-sectional view taken along plane 3—3 of FIG. 1.

Turning to FIG. 1, a side cross-sectional view of an oxygenator 10 is shown. The major components are an inflatable balloon 20 and a number of gas passageways 14 which substantially surround the balloon 20. In the one preferred embodiment, these gas passageways are a multitude of hollow gas-permeable fibers or tubules. The fibers 14 are formed into loops, as shown in FIGS. 1-3, that substantially surround and cover the exterior surface of balloon 20. The gas-permeable walls of the fibers 14 provide a large total surface area for diffusion of oxygen into the blood stream, and diffusion of carbon dioxide out of the blood stream. Any of a variety of flexible, hollow, gas-permeable fibers currently available on the market, such as Mitsubishi KPF190M polypropylene fibers, are suitable for this purpose. To provide a true ideal membrane, the polypropylene fibers should be coated with silicone rubber and bonded with a non-thrombogenic component.

The balloon 20 and fiber loops 14 of the device are implanted in the venous system of the patient through a single small incision. For example, the device 10 can be implanted through the right interior jugular vein into the superior vena cava of a patient. For maximum effectiveness, the balloon 20 and fiber loops 14 are fully inserted through the incision up to the level of the connector 12. Insertion of the balloon 20 and fiber loops 14 can be aided by using a conventional introducer similar to the type presently employed to insert a cardiac pacemaker.

Figures 4, 5:
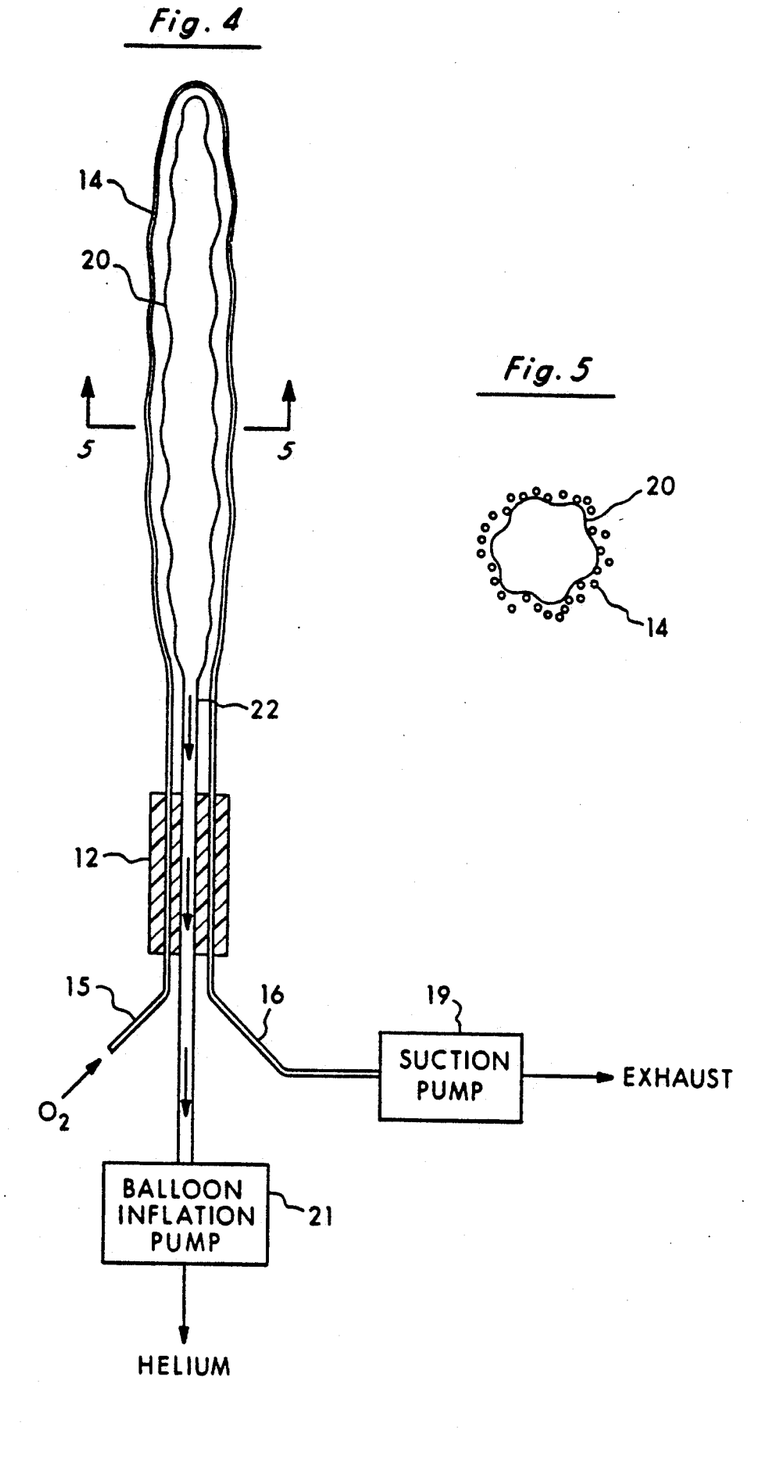
FIG. 4 is a side cross-sectional view corresponding to FIG. 1 in which the balloon has been deflated.
FIG. 5 is another cross-sectional view taken along plane 5—5 of FIG. 4.

The connector 12 provides separate lumens to supply and exhaust the fiber loops 14 and for inflation of the balloon 20. An external pump 21 is connected to the balloon inflation lumen 22 of the connector 12 and can be used to repeatedly inflate and deflate the balloon 20 at a predetermined frequency. A frequency of approximately one cycle per second has been experimentally demonstrated to provide satisfactory results in minimizing streaming and maintaining a turbulent flow of blood adjacent to the oxygenator. Any gas or fluid can be pumped into and released from the balloon for this purpose. However, helium offers the advantages of having very low viscosity and density for ease of pumping, and is quickly dissolved in the bloodstream in the event helium bubbles leak from the device. In the preferred embodiment, at least a portion of the fiber loops 14 are secured to the exterior surface of the inflation balloon 20 (e.g. by adhesive bonding). This helps to insure that expansion and contraction of the balloon 20 causes movement of the fibers 14 within the blood vessel. FIGS. 1 and 2 provide cross-sectional views of the oxygenator 10 with the balloon 20 fully inflated. In comparison, FIGS. 4 and 5 show the same oxygenator with the balloon 20 deflated.

After the device has been implanted, a supply of oxygen-containing gas is connected to the second lumen 15 of the connector 12. The oxygen flows through second lumen 15 into the fiber loops 14. Oxygen flows along the interior passageways of the fibers 14 and diffuses outward through the gas-permeable walls of the fibers into the surrounding blood stream. Carbon dioxide also diffuses inward from the blood stream through these gas-permeable walls into the interior of the fibers. Carbon dioxide and any remaining oxygen in the fibers are vented to the atmosphere at the distal ends of the fibers through a third lumen 16 in the connector 12. Negative pressurization can be applied by means of a suction pump 19 connected to the third lumen 16 to enhance gas flow through the fiber loops.

It should be noted that the present invention can also be used to administer anesthetic gases or other medications directly into the patient's blood system. For this purpose, a mixture of oxygen and anesthetic gases flow through the fiber loops of the device and diffuse into the patient's blood stream.

Figure 6:
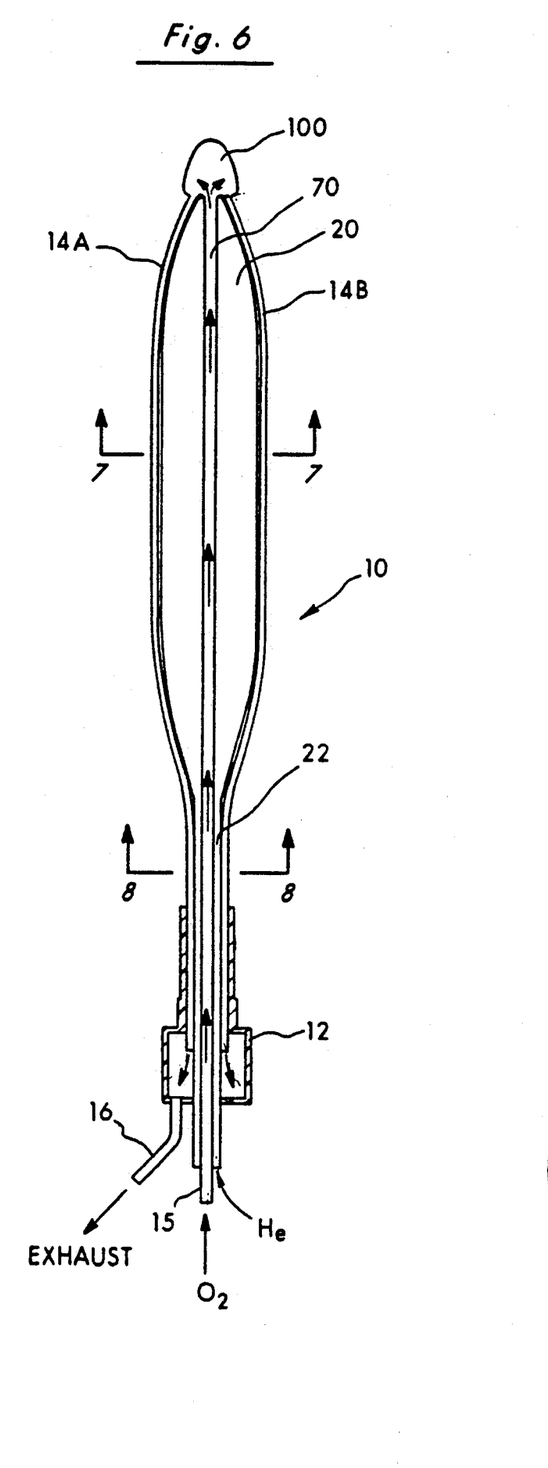
FIG. 6 is a side cross-sectional view of an alternative embodiment of the present invention having a central oxygen supply tube and a hollow tip member.
Figure 7:
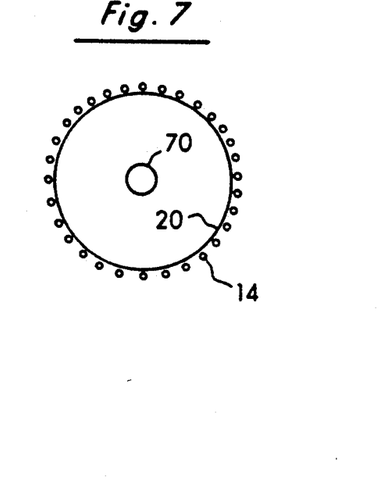
FIG. 7 is another cross-sectional view taken along plane 7—7 of FIG. 6.
Figure 8:
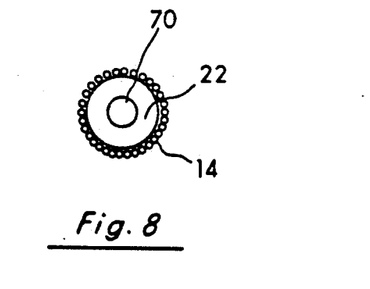
FIG. 8 is another cross-sectional view taken along plane 8—8 of FIG. 6.

FIGS. 6, 7, and 8 show an alternative embodiment of the oxygenator in which a hollow tip member 100 has been added at the distal end of the balloon 20. A central oxygen supply tube 70 extends through the connector 12 and the balloon 20 to the interior of the tip member 100. Each of the fiber loops is bisected at its distal point into two arms 14a and 14b. The resulting ends of the fibers are sealed in fluid communication with the internal cavity of the tip 100. The tip member 100 can be molded from plastic or rubber around the ends of the fibers to prevent the escape of gases at the junction between the fiber ends and the tip member 100. The tip can also be shaped with a tapered contour to ease insertion of the device through an incision. Thus, in this embodiment, oxygen-containing gases flow from an external supply through the oxygen supply tube 70, into the internal cavity of the tip member 100, through both arms 14a and 14b of the fibers, and are then exhausted through the exhaust lumen 16 in the connector 12, as previously described. It should be noted that the oxygen supply tube 70 and the balloon inflation lumen 22 can be formed as concentric tubes as shown in FIGS. 6 and 8. A cross-sectional view of the upper portion of the balloon 20 and the oxygen supply tube 70 is provided in FIG. 7. The oxygen supply tube 70 also acts as a structural support for the tip member 100 and fiber loops 14, and provides a degree of rigidity to aid initial insertion of the device into the blood vessel.

Figure 9:
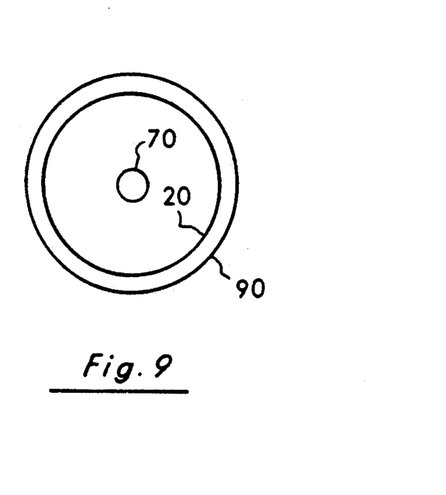
FIG. 9 is a cross-sectional view of alternative embodiment in which the hollow fibers surrounding the inflation balloon are replaced with a single gas-permeable membrane.

FIG. 9 discloses another alternative embodiment in which the fibers 14 have been replaced by a single gas-permeable membrane 90 surrounding the inflation balloon 20. The resulting structure is essentially a balloon within a balloon. As before, oxygen-containing gas is supplied through the oxygen supply tube 70 to the tip member 100. The oxygen then flows from the tip member 100 back toward the connector 12 through the annular space between the inflation balloon 20 and the outer gas-permeable membrane 90. Cross-diffusion of oxygen and carbon dioxide occurs across the gas-permeable membrane between the annular space and the patient's bloodstream, as previously discussed. Repeated inflation and deflation of the inflation balloon 20 causes corresponding movements in the gas-permeable membrane 90 to minimize streaming. In yet another alternative embodiment, the gas-permeable membrane 90 can be tacked to the exterior surface of the inflation balloon 20 along a number of longitudinal lines to define a plurality of gas passageways extending from the tip member 100 to the connector 12.

Figure 10:
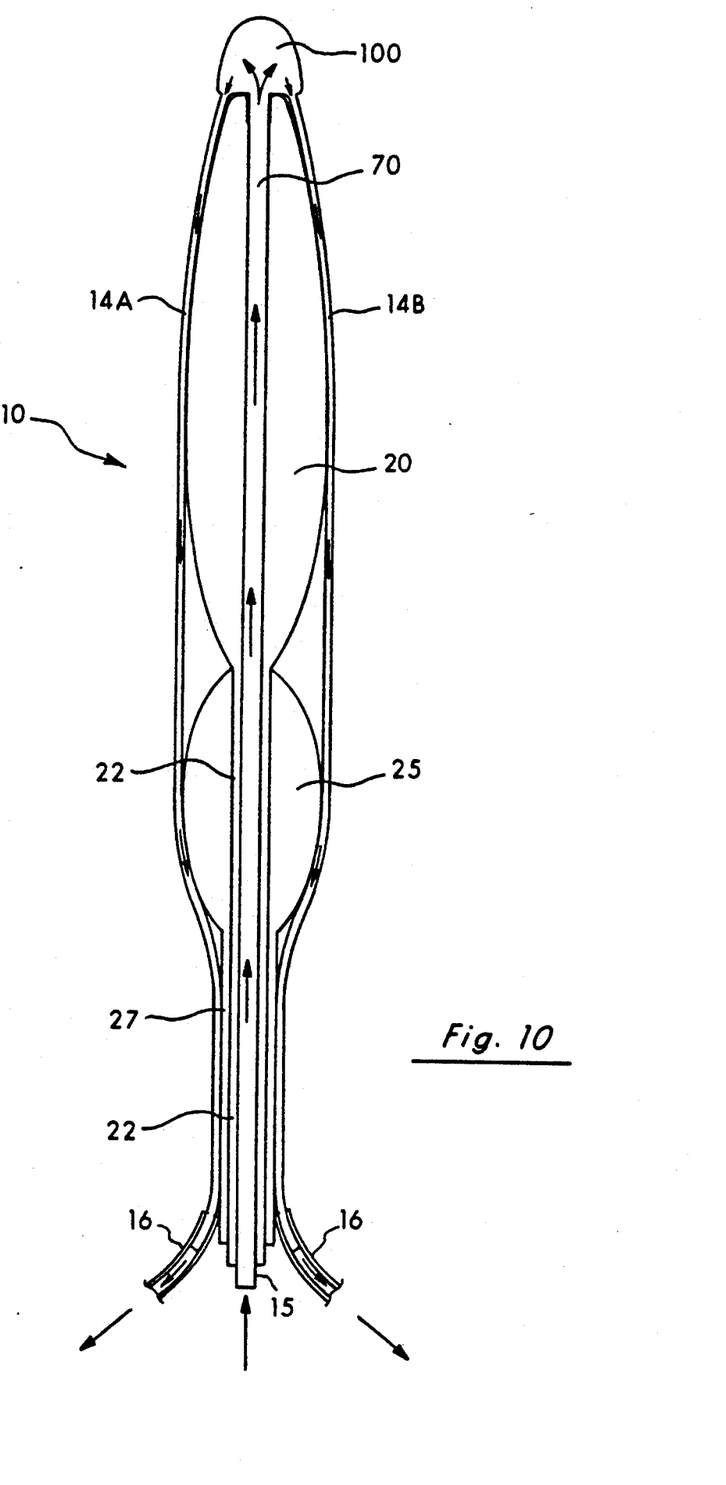
FIG. 10 is a cross-sectional view of yet another alternative embodiment in which two balloons are inflated and deflated asynchronously.

FIG. 10 shows yet another alternative embodiment of the present invention in which a second inflation balloon 25 has been added adjacent to the first inflation balloon 20. This second balloon 25 has a separate lumen 27 extending through the connector 12 to permit separate inflation and deflation of the second balloon 25 independent of the first balloon 20. In this embodiment, the balloons 20 and 25 will typically be inflated asynchronously (i.e., out of phase with one another) so that resulting turbulence in the patient's bloodstream is maximized.

Figures 11, 12, 13:
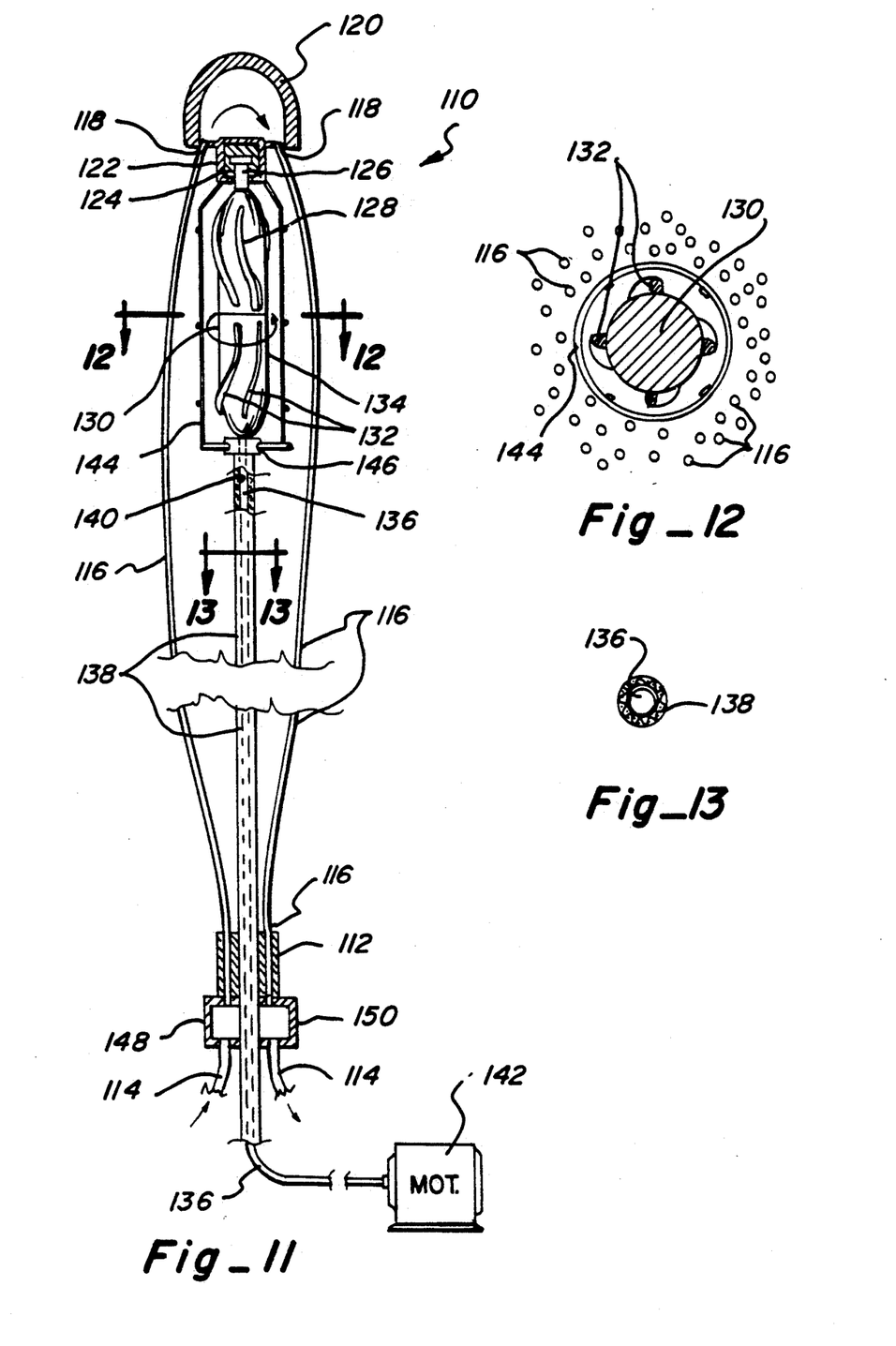
FIG. 11 is a cross-sectional view of the embodiment of the invention wherein a rotating blade is positioned within the loops formed by the hollow fibers to disrupt the flow of blood past the oxygenator.
FIG. 12 is a section taken along line 12—12 of FIG. 11.
FIG. 13 is section taken along line 13—13 of FIG. 11.

Still another embodiment 110 of the invention is shown in FIGS. 11-13 wherein a connector 112 is adapted to receive and retain the proximal ends 114 of a plurality of fibers 116 which in combination form continuous loops by having their opposite or distal ends 118 secured in communication with a hollow tip 120 of the oxygenator. There are, of course, numerous fibers 116 even though only two such fibers are shown in FIG. 11 as completing one loop. The tip 120 has a recessed pocket 122 formed in a trailing end thereof with the pocket receiving a bearing member 124 that in turn rotatably supports and confines a shaft 126 on the distal end of an agitating member 128.

The agitating member 128 includes a rotating head 130 having a plurality of curved blades 132 protruding substantially radially from a main body 134 of the head. The head has its proximal end unitarily fixed to a flexible but rotatable cable 136 that is rotatably housed in a flexible sleeve 138. The sleeve 138 passes from the head 130 through a central passage 140 in the connector to an electric motor 142. The electric motor can be a unidirectional motor having its output shaft unitarily fixed to the rotatable cable 136 so that energization of the motor causes the cable to rotate thereby rotating the head 130 whose distal end is rotatably supported by the hollow tip 120.

The hollow tip 120 further supports a generally cylindrical cage 144 that is slightly larger in diameter than the diameter of the head 130 so that the head is free to rotate internally of the cage. A proximal end of the cage is connected by a collar 146 to the distal end of the flexible sleeve 138.

It will be appreciated that the cage 144 separates the fibers 116 from the rotatable head 130 to prevent the fibers from being entangled in the blades 132 of the head. The blades on the head are curved in a substantially spiral fashion with blades on a distal half of the head being a mirror image of blades on a proximal half of the head.

In this manner, rotation of the head will cause the blades to interface with the linear flow of blood through the blood vessel so that the blood is thrown substantially radially outwardly in two opposite directions. In other words, the blades 132 on the proximal end of the head will throw the blood in one swirling but substantially radial direction while the blades at the distal end of the head will throw the blood in a substantially radial but opposite swirling direction.

Half of the fibers 116 at their proximal end 114 are connected through a manifold 148 to a source of oxygen while the other half of the fibers at their proximal end are connected through a manifold 150 to a source of vacuum so that low pressure oxygen can be drawn through the fibers in a complete loop commencing at the proximal end 114 of half the fibers and terminating at the proximal end 114 of the other half of the fibers.

In operation of this embodiment of the oxyqenator, after the oxygenator has been inserted into the blood vessel up to the location of the connector 112, the motor is energized to start the heads rotating so that the blades will disrupt the linear flow of the blood and move the blood radially outwardly in swirling convective flow patterns thereby forcing the fibers surrounding the blades into continual movement to optimally expose the surface area thereof to the blood thereby maximizing the cross diffusion of gases in and out of the fibers. While the rotational speed of the head may vary, it is suggested that it be rotated about 10,000 rpm. In a preferred use of the device, oxygen is introduced to the fiber loops at a flow rate of approximately 1 to 3 liters per minute and at a nominal pressure of approximately 6 to 15 mmHg. A suction pressure of approximately $-150$ to $-250$ mmHg is applied at the opposite end of the fiber loops.

Another embodiment 152 of the oxygenator of the present invention is illustrated in FIGS. 14–17. This embodiment which might be referred to as an electromagnetic embodiment has a different system for moving fibers 154 to optimize the cross-diffusion of gases through the walls of the fibers. As in the embodiment described in FIGS. 11–13, there are a plurality of fibers 154 having their proximal ends 156 secured in a connector 158 and having their distal ends 160 secured to a hollow tip 162 so as to establish continuous loops projecting from the connector 112 which can be inserted into a blood vessel. The connector has two separated manifolds 164 and 166 so that the proximal end of one half of the fibers communicate with one manifold 164 while the proximal end of the other half of the fibers communicate with the other manifold 166. One manifold 164 has an inlet connected to a source of oxygen while the other manifold 166 has an outlet connected to a source of vacuum so that oxygen can be drawn into the fibers and after cross-diffusion, $CO_2$ can be removed from the fibers by the vacuum source.

Figures 14, 15, 16, 17:
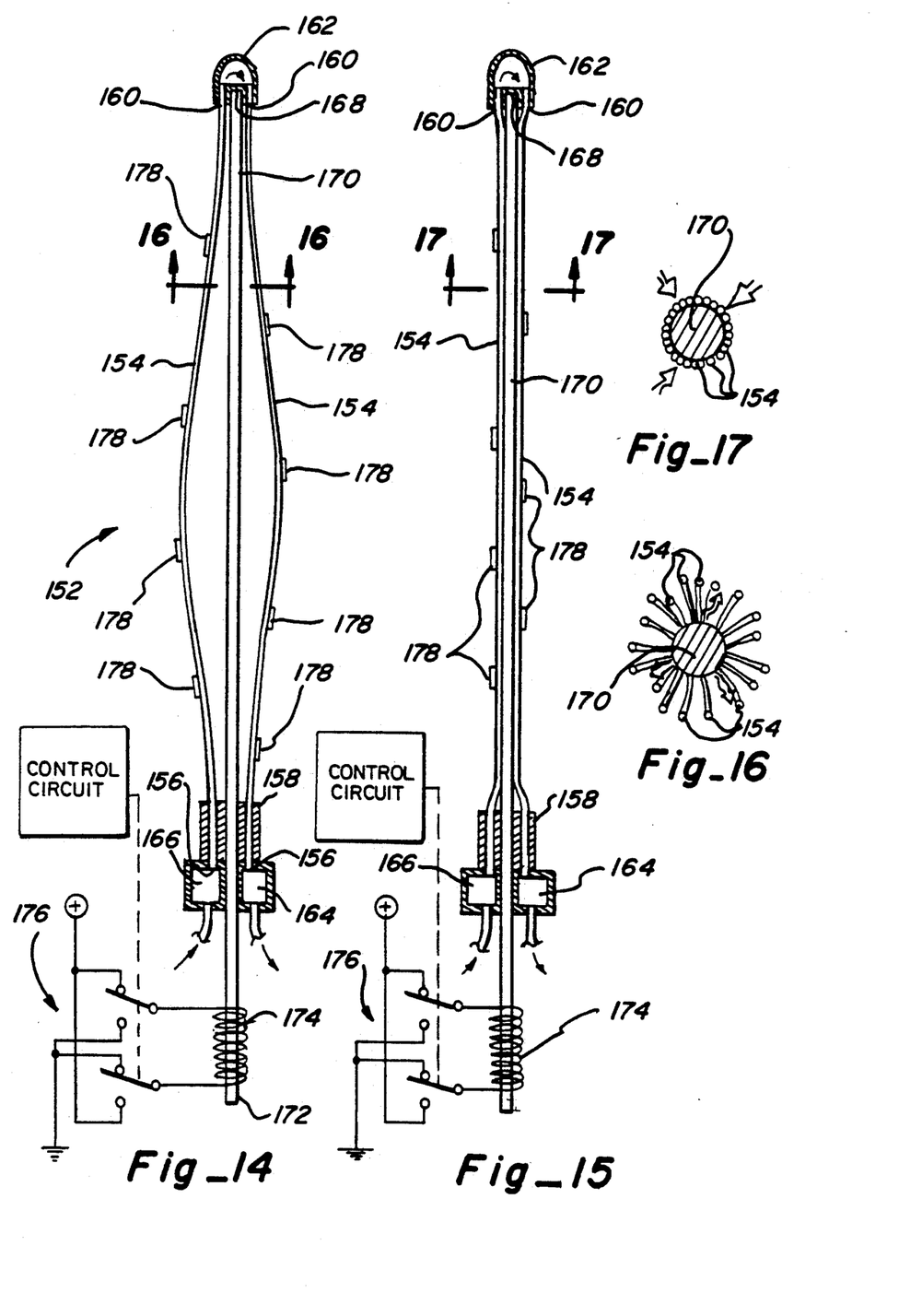
FIG. 14 is a cross-sectional view of still another embodiment of the invention wherein an electromagnetic system is employed for attracting the looped fibers to a magnet core with the fibers shown in a spaced relationship with the core.
FIG. 15 is a cross-sectional view similar to FIG. 14 with the fibers drawn closely adjacent to the magnetic core.
FIG. 16 is a section taken along line 16—16 of FIG. 14.
FIG. 17 is a section taken along line 17—17 of FIG. 15.

The hollow tip 162 has a recessed pocket 168 formed in a trailing end thereof which is adapted to receive and retain the end of an elongated magnetizable rod 170 which may be made out of any suitable soft metal. The rod 170 is flexible as are the fibers 154 so that the entire device can be inserted into a blood vessel without damaging the vessel.

The proximal end 172 of the rod which is positioned outside of the body of the patient during use of the device has a coil 174 wrapped therearound with the coil being connected to a source of DC current through a suitable switching system 176. The switching system is designed so that the direct current can be alternately passed through the coil in opposite directions thereby reversing the polarity of the rod.

The fibers 154 are provided with a paramagnetic substance such as a polymer so that they can be attracted to or repelled from the rod depending upon its magnetized polarity. The paramagnetic material can either be integrated directly into the material from which the fibers are made or it might be applied to the surface of the fibers as by spot painting at spaced locations 178 along the length of the fibers.

As will be appreciated, in operation of the device, when the rod 170 is magnetized in a first polarity, the fibers 154 are attracted thereto as shown in FIGS. 15 and 17 and when the polarity is reversed by throwing the switching system 176 in the opposite direction, the fibers are repelled as illustrated in FIGS. 14 and 16. As can be appreciated, alternate switching of the switching system causes the fibers to move inwardly and outwardly thereby preventing the blood from streaming past the oxygenator. In this manner, the fibers can be optimally presented to the blood to expose maximum surface area of the fibers for optimal cross-diffusion of the oxygen and $CO_2$ gas. The operating parameters as relates to gas pressures and flow rates would preferably be the same as for the embodiment shown in FIGS. 11–13.

In an alternate embodiment which would be identical to the embodiment illustrated in FIGS. 14–17 except switching system would be modified, the rod would be alternately magnetized and demagnetized. The switching system would be arranged so that current could be passed through the coil or not whereby upon energization of the coil and thus magnetization of the rod, the fibers would be attracted to the rod but upon de-energization of the coil and thus demagnetization of the rod, the fibers would be allowed to free float in a natural state which resembles the orientation of the fibers as illustrated in FIG. 14. The operating parameters would not change from that used in connection with the embodiment of FIGS. 14–17.

Although the present invention has been described with a certain degree of particularity, it is understood that the present disclosure has been made by way of example, and changes in detail or structure may be made without department from the spirit of the invention, as defined in the appended claims.

I claim:

1. A percutaneous oxygenator for insertion into a blood vessel comprising:
   a plurality of hollow gas permeable fibers forming loops for at least partial insertion into a blood vessel, said fibers being adapted to permit diffusion of gases between said blood vessel and the interior of said hollow fibers,
   a connector means having said fibers connected thereto such that the fibers extend away from the connector means,
   liquid agitation means positioned in said vessel and within said loops of the hollow fibers, and
   power means operatively connected to said agitation means to drive the agitation means in a manner to disrupt the flow of blood through said vessel and enhance the flow of blood around said fibers.

2. The oxygenator of claim 1 wherein said liquid agitation means consists of a blade adapted to be selectively rotated by said power means.

3. The oxygenator of claim 2 wherein said blade is configured such that upon rotation by said power means the blood flowing through said blood vessel is substantially redirected radially outwardly from said blade toward the looped fibers.

4. The oxygenator of claim 3 wherein said blade has curved axially displaced segments of substantially opposite curvature.

5. The oxygenator of claim 2 wherein said power means includes a motor positioned outside the body containing said blood vessel and further includes a flexible drive cable connecting the motor to the blade.

6. The oxygenator of claim 5 wherein said cable is rotatably disposed in a flexible sleeve.

7. The oxygenator of claim 6 wherein said sleeve extends through said connector.

8. The oxygenator of claim 2 further including a cage operatively connected to said blade to prevent interference between said blade and said fibers.

9. The oxygenator of claim 8 further including a hollow tip to which said fibers are connected in fluid communication at a remote location from said connector and wherein said tip supports said cage and said blade.

10. A percutaneous oxygenator for insertion into a blood vessel comprising:
    a plurality of hollow gas permeable fibers forming loops for at least partial insertion into a blood vessel, said fibers having a paramagnetic substance thereon and being adapted to permit diffusion of gases between said blood vessel and the interior of said hollow fibers,
    a connector means having said fibers connected thereto such that the fibers extend away from the connector means,
    an electromagnet means at least partially positioned in said vessel and within said loops of the hollow fibers, and
    electric power means operatively connected to said electromagnet means to move said fibers upon selective energization of said magnet.

11. The oxygenator of claim 10 wherein said electromagnet includes an elongated flexible magnetizable rod and a coil surrounding said rod along a portion of its length, said coil being operatively and selectively connected to a source of electric energy.

12. The oxygenator of claim 11 wherein said coil and source of electric energy are positioned outside the body containing said blood vessel.

13. The oxygenator of claim wherein said paramagnetic substance is integrated into the material from which the fibers are fabricated.

14. The oxygenator of claim 13 wherein said paramagnetic substance is a polymer.

15. The oxygenator of claim 11 wherein said paramagnetic substance is affixed to said fibers at spaced locations along the length of the fibers.

16. The oxygenator of claim 11 wherein said paramagnetic substance is spot painted onto said fibers.

17. The oxygenator of claim 11 further including a hollow tip to which said fibers are connected at a remote location from said connector, said tip supporting an end of said rod.

18. The oxygenator of claim 11 wherein said coil is operatively connected to said source of electric energy through a switch mechanism for alternatively changing the polarity of said rod to alternately attract and repel said fibers.

* * * * *

UNITED STATES PATENT AND TRADEMARK OFFICE
CERTIFICATE OF CORRECTION

PATENT NO. : 5,271,743

DATED : Dec. 21, 1993

INVENTOR(S) : Brack G. Hattler

It is certified that error appears in the above-identified patent and that said Letters Patent is hereby corrected as shown below:

Cover Page, line 4 item [56] References Cited:     "--Homopump--" should read -- Hemopump --

Column 8, line 56:     "--except--" should read -- except that the --

Column 10, line 28:     "--claim--" should read -- claim 11 --

Signed and Sealed this

Seventeenth Day of May, 1994

*Attest:*

BRUCE LEHMAN

*Attesting Officer*     *Commissioner of Patents and Trademarks*